United States Patent [19]

Cuypers

[11] Patent Number: 5,396,886

[45] Date of Patent: Mar. 14, 1995

[54] METHOD FOR PREDICTING CORONARY HEART DISEASE

[75] Inventor: Dirk Cuypers, Bogaarden, Belgium

[73] Assignee: Bristol-Myers Squibb Company, Princeton, N.J.

[21] Appl. No.: 84,105

[22] Filed: Jul. 1, 1993

[30] Foreign Application Priority Data

Oct. 2, 1992 [EP] European Pat. Off. ........... 92116918

[51] Int. Cl.$^6$ .............................................. A61B 5/00
[52] U.S. Cl. .................................... 128/630; 128/898
[58] Field of Search ............... 128/630, 668, 670, 671, 128/695, 897, 898; 283/117, 900

[56] References Cited

U.S. PATENT DOCUMENTS

| | | |
|---|---|---|
| 3,811,040 | 5/1974 | Weinfurt et al. |
| 4,346,697 | 8/1982 | Cohen ............................ 128/630 X |
| 4,464,122 | 8/1984 | Fuller et al. .................... 128/630 X |
| 4,930,519 | 6/1990 | Anderson et al. ............... 128/719 X |
| 5,265,605 | 11/1993 | Afflerbach ........................ 128/630 |

FOREIGN PATENT DOCUMENTS

| | | | |
|---|---|---|---|
| 2348582 | 4/1974 | Germany . | |
| 9201418 | 2/1992 | WIPO ............................... | 128/630 |

OTHER PUBLICATIONS

Erica Research Group, "Prediction of coronary heart disease in Europe" European Heart Journal (1991) 12, 291–297.

Brook, J. G. et al "Cholesterol and coronary heart disease prevention—A transatlantic consensus", Eur. Heart Journal (1989) 10, 702–711.

Grundy, S. M. "Cholesterol and Coronary Heart Disease" Jama, Nov. 1986, vol. 256: 2849–2858.

Assmann, G. et al "The Prospective Cardiovascular Munster Study: Prevalence and Prognostic Significance of Hyperlipidemia in Men with Systemic Hypertension", Am. J. Card. 1987; 59:9G–17G.

Egan, B. M. et al "Comparative Effects of Overweight on Cardiovascular Risk in Younger Versus Older Men", Am. J. Card., Feb. 1991, vol. 67: 248–252.

Kannel, W. B. "Office assessment of coronary candidates and risk factor insight from the Framingham study", J. of Hypertension 1991, 9 (Suppl. 7): S13–S19.

Anderson, K. M. et al "An Updated Coronary Risk Profile", Circulation, vol. 83, No. 1, Jan. 1991: 356–362.

"Prediction of coronary heart disease in Europe. The 2nd report of the WHO-ERICA Project", European Heart Journal (1991) 12, 291–297.

Primary Examiner—Lee S. Cohen
Assistant Examiner—Samuel Gilbert
Attorney, Agent, or Firm—Burton Rodney

[57] ABSTRACT

A device or system is provided for calculating and visualising the risk for developing coronary heart disease which is in the form of a cardiovascular risk diagram which includes a series of cardiovascular risk scales projected on cardiovascular risk areas (for example, delineated by different colours) each scale representing a different cardiovascular risk factor. Data for each cardiovascular risk is recorded on its appropriate risk scale, and data points-on adjacent risk scales are connected to form enclosed area superimposed over the risk areas. The resulting enclosed area is visually or otherwise compared to the total area of all cardiovascular risk areas, to determine a score of cardiovascular risk.

6 Claims, 3 Drawing Sheets

METHOD FOR PREDICTING CORONARY HEART DISEASE

FIELD OF THE INVENTION

The present invention relates to a system and method for the visualisation of different cardiovascular risk factors on a scale, projected in different risk areas, to give a cardiovascular risk diagram which can be used to predict coronary heart disease.

BACKGROUND OF THE INVENTION

The major risk factors for coronary artery diseases are widely recognised. Age and gender have a powerful effect, but are immutable. Hypertension, cigarette smoking, total cholesterol and low density lipoprotein cholesterol double or more the risk.

Other important recognised risk factors are overweight, left ventricular hypertrophy, glucose intolerance, hyperinsulinaemia and physical inactivity (Brach, Cholesterol and coronary heart disease prevention. A transatlantic consensus. European Heart Journal, 1989, 10:702–711; Grundy, Cholesterol and coronary heart disease. Jama, November 1986, Vol. 256:2849–2858; The prospective cardiovascular Munster study: Prevalence and prognostic significance of hyperlipidemia in men with systemic hypertension. Am. J. Card., 1987, 59:9G–17G; Egan et al., Comparative effect of overweight on cardiovascular risk in younger versus older men. Am. J. Card., February 1991, Vol. 67:248–252).

Further epidemiological studies have shown that for some cardiovascular diseases such as hypertension, assessment requires consideration of a multivariate risk profile (W. Kannel et al., Office assessment of coronary candidates and risk factor insights from the Framingham study. J. of Hypertension, 1991, 9 (Suppl. 7):S13–S19; K. Anderson et al., An updated coronary risk profile. Circulation, Vol. 83, n° 1, January 1991: 356–362; Prediction of coronary heart disease in Europe. WHO-Erica Project, Erica Research Group, The 2nd European Heart Journal (1991) 12:291–297).

Before starting any therapy for treating coronary artery disease, a complete assessment of overall cardiovascular risk factors is essential. Unfortunately, even where all such cardiovascular risk factors are recorded, there is no existing system for correlating these risk factors with probability of developing coronary heart disease.

The American Heart Association (AHA) (K. Anderson et al., supra) and the WHO-Erica Project (Erica Research Group, supra) give different cardiac heart disease equations to predict the risk for developing coronary heart diseases. However, these mathematical formulas do not provide visualisation of the cardiovascular risks.

It is therefore apparent that there is a need for a device and method to visualise the most important risk factors for each patient for the benefit of the physician and the patient. An object of the present invention is to create a "Cardiovascular Risk Manager (CVRM)". Such a system could be used to evaluate the cardiovascular patient, to estimate his risk profile, to decide the therapeutic approach, and/or to increase the therapeutic compliance of the patient.

DESCRIPTION OF THE INVENTION

In accordance with the present invention, a cardiovascular risk device for delineating cardiovascular risk factors, which is used for predicting development of coronary heart disease in a patient, is provided, which is in the form of a diagram (which as will be seen hereinafter is preferably in the form of a circle) including a series of cardiovascular risk areas delineating low to high risk areas; a series of cardiovascular risk scales delineating low to high risk for various cardiovascular risk factors, superimposed over said cardiovascular risk areas, so that the cardiovascular risk factor delineated by each scale is correlated in degree of risk with the cardiovascular risk area over which it is superimposed. The numerical value of each of the cardiovascular risk factors of a patient represented on the cardiovascular risk scales, is marked on the appropriate cardiovascular scale as a data point, and the data points on adjacent cardiovascular risk scales are connected to form an enclosed area superimposed on said cardiovascular risk areas. The so-delineated enclosed area superimposed on the cardiovascular risk areas is compared to the total area of all cardiovascular risk areas (in the preferred embodiment being the total area of the circle) to determine a score or probability of cardiovascular risk which is used to predict development of coronary heart disease.

In a preferred embodiment of the invention, the series of cardiovascular risk areas is depicted as a circle and is formed of a series of concentric cardiovascular risk areas within the circle, which may be delineated by different shades and/or colours; and the series of cardiovascular risk scales is formed of an array of scales radially extending outwardly from a central point of the series of concentric cardiovascular risk areas. Each of the cardiovascular risk scales represents a different cardiovascular risk factor. The cardiovascular risk scales are preferably formed of radially extending axes or spokes projected over the concentric cardiovascular risk areas, converging at the central point of the concentric cardiovascular risk areas.

In the preferred embodiment of the invention, the most external concentric cardiovascular risk area represents the normal risk area, so that projected data on the cardiovascular risk scales which fall on the normal risk area are to be considered as normal values; the innermost concentric cardiovascular risk area is the highest risk area, so that projected data on the cardiovascular risk scales which fall in the highest risk area are considered as high risk values; and the concentric cardiovascular risk area(s) between the normal risk or outermost area and the highest risk or innermost area, are elevated risk areas. Each of the cardiovascular risk areas are preferably delineated by different colours and/or shades or by other visual means such as cross-hatching, pin-points and the like.

It will be appreciated that the cardiovascular risk areas may, in addition to being a plurality concentrically disposed areas, take the form of a series of other shaped areas superimposed on each other such as rectangular areas, square areas and the like.

It is preferred that the cardiovascular risk scales extend across such risk areas starting from a common central point disposed within the smallest risk area.

The cardiovascular risk factors represented by the cardiovascular risk scales include one or more of age, weight, blood pressure (systolic and diastolic), lipid parameters including total cholesterol, triglycerides, low and/or high density lipoproteins, glycemic parameters and/or smoking habits. For example, in a preferred embodiment of the invention, the cardiovascular risk factors represented by the cardiovascular risk scales include age (years), systolic pressure (mmHg), diastolic pressure (mmHg), weight (kg or lb), LDL-cholesterol or HDL-cholesterol (mg/dl), triglycerides (mg/dl), smoking (number of cigarettes per day).

In addition, in accordance with the present invention, there is provided a method for predicting coronary heart disease employing the cardiovascular risk device as defined above. The method of the invention is designed for calculating and visualising the risk of developing coronary heart disease, and includes the steps of providing a diagram, which preferably is in the form of a circle, which includes a series of cardiovascular risk areas delineating low to high cardiovascular risk areas and a series of cardiovascular risk scales for various cardiovascular risk factors, delineating low to high cardiovascular risk for each risk factor, superimposed over the cardiovascular risk areas; determining a numerical value for each cardiovascular risk factor, of a patient, represented on the cardiovascular risk scales; recording such numerical value on the appropriate cardiovascular risk scale as a data point; connecting data points on adjacent cardiovascular risk scales to form an enclosed area superimposed on the cardiovascular risk areas (preferably a circle), comparing the so-delineated enclosed area superimposed on the cardiovascular risk areas with the total area (for example, the area of the circle) to determine a score of cardiovascular risk used to predict development of coronary heart disease.

DETAILED DESCRIPTION OF THE INVENTION

Figure 1:
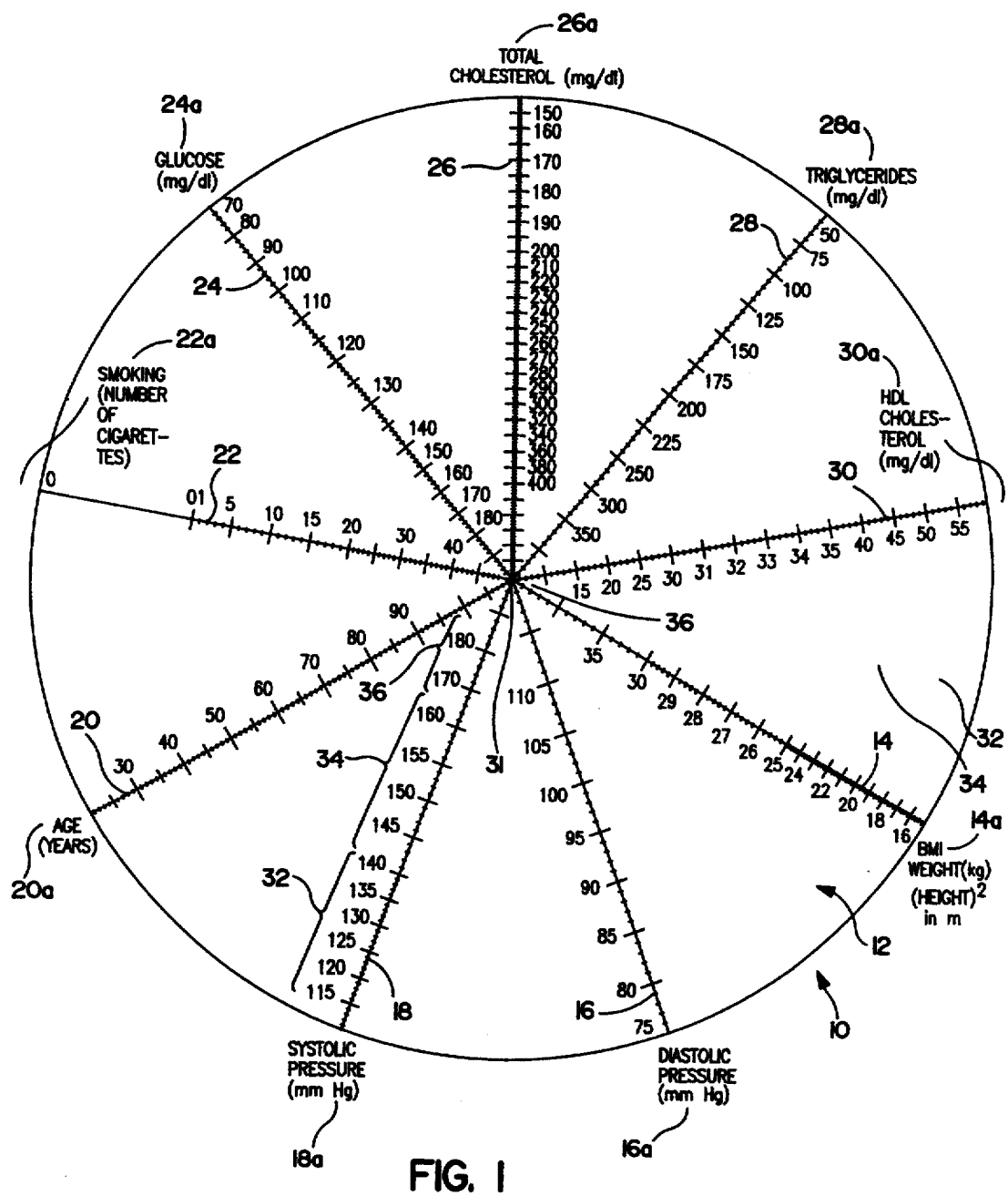
FIG. 1 is a graphic view of a cardiovascular risk diagram in accordance with the present invention.

Referring to the accompanying Figures, wherein like numerals represent like components in the two views, the cardiovascular risk device 10, in accordance with the present invention, is an integrated diagram or system of a pictorial representation of a patient's cardiovascular risk profile on paper. As shown in FIG. 1, the device 10 is formed of a series of cardiovascular risk scales or axes 14 to 30, for various cardiovascular risk factors 14a to 30a, superimposed over a series of cardiovascular risk areas 32, 34, 36 as may be designated by different shades and/or colours. Each axis, 14 to 30, corresponds to a cardiovascular risk parameter 14a to 30a, respectively.

Physically, the axes are subdivided in three areas each corresponding to a cardiovascular risk area such as, for example, designated by the following: dark (such as green) outer area 32 (no risk); light (such as orange) middle area 34 (moderate risk); or dark (such as red) inner area 36 (high risk).

The cardiovascular risk factors which may be expressed on the cardiovascular risk device of the invention include, but are not limited to, age, weight parameters, diastolic and systolic blood pressure, left ventricular hypertrophy, lipid parameters such as total cholesterol, triglycerides, high density lipoproteins and/or low density lipoproteins, glycemic parameters, smoking habits and the like. The above risk factors may be expressed as actual values logarithmically, or as a percentage of a reference value on the cardiovascular risk scales superimposed or projected on areas of the device which represent different risk areas, the number of which are a function of defined risk areas. The risk areas can be symbolically presented as concentric areas, polygonal areas such as square or rectangular areas, and the like.

The combination of the cardiovascular risk factors on the cardiovascular scales or axes superimposed on the cardiovascular risk areas provides the cardiovascular risk device of the invention. The cardiovascular risk device of the invention may be presented by any audio-visual method, such as paper, computer screen and the like.

The value obtained for a specific risk factor of a patient can be registered on a cardiovascular risk scale. The units for each scale are a function of the value the physician will use.

Figure 2:
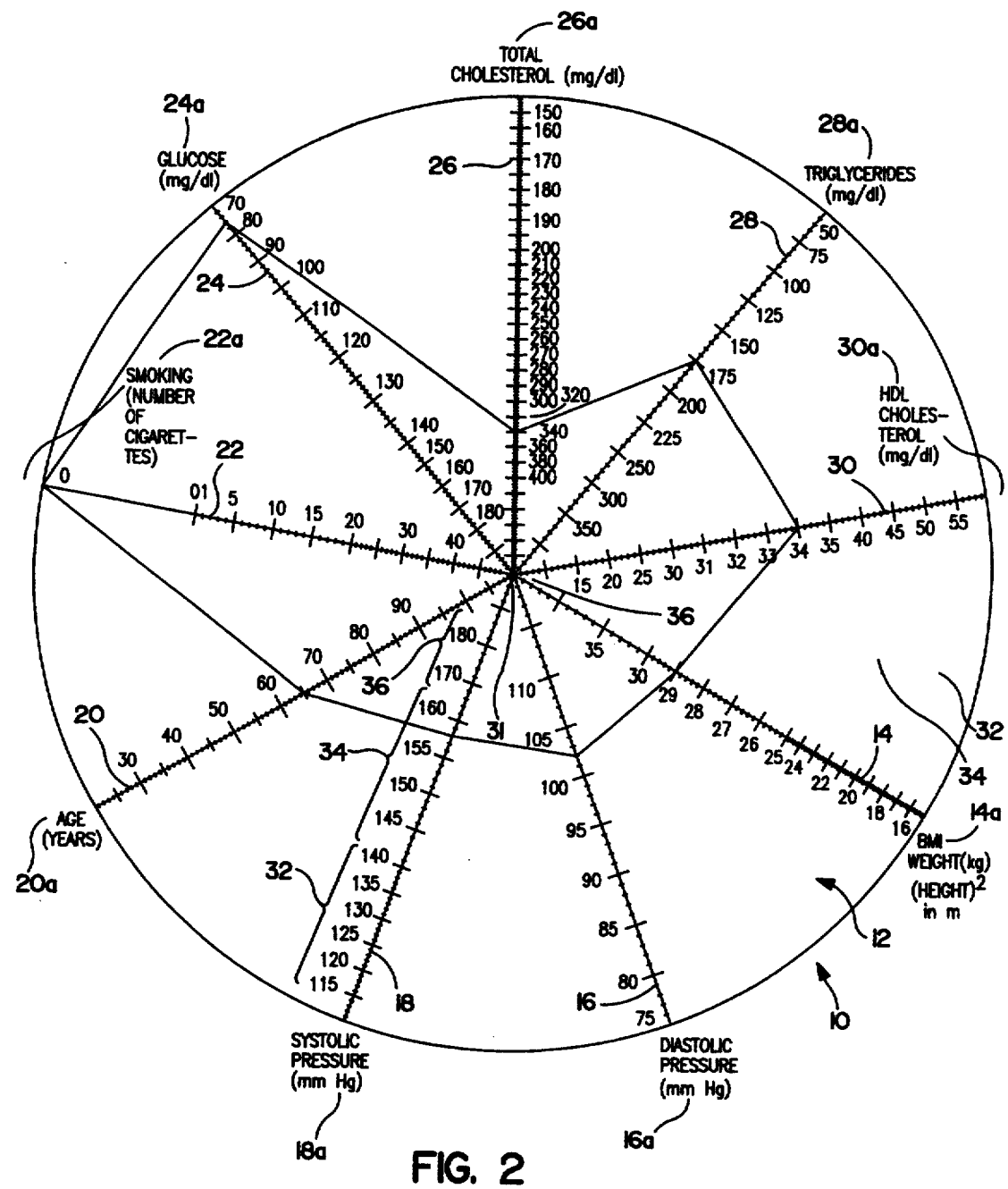
FIG. 2 is a graphic view of a cardiovascular risk diagram in accordance with the invention which includes a polygonic graphic presentation of the cardiovascular risk factors of a patient.

The polygonal surface area 40 formed by connecting data points of the cardiovascular risk scales as shown in FIG. 2 represents a risk profile which may be compared against the total area of the circle, such as the area of the circle at the outer inner limits of outer risk area 32, to obtain a score.

It will be appreciated that the cardiovascular risk axes or scales may be calibrated so that the high risk area is the inner cardiovascular risk area (such as 32) and the low risk area is the outer cardiovascular risk area (such as 36). In such case, the smaller the polygonal area 40 of the patient, the greater risk of developing coronary heart disease.

The cardiovascular risk device of the invention can also be used for clinical/epidemiological purposes.

The device of the invention can be used as a record form for the follow-up of clinical studies to evaluate specific cardiovascular risk factors. Indeed, the device of the invention can be coded as such, that reading of the axes can be done manually or electronically.

The cardiovascular risk device and method of the invention can also be adapted to be performed with the help of a computer program, wherein the different cardiovascular risk factors will be entered into the computer system and on that basis an individual cardiovascular risk diagram will be generated and the total risk factor will be calculated. This procedure has the advantage that the number and selection of the risk factors can easily be varied, depending on the needed therapy. For the purpose of comparison, however, only diagrams consisting of the same number, selection and geometrical arrangement of the scales representing the risk factors should be used.

The cardiovascular diagram can also be visualized by a display means such as LEDs which are so connected that the entered risk factors automatically cause displaying of the cardiovascular risk diagram.

As seen, the device of the present invention allows for the visualization of any cardiovascular risk factor on scales projected on risk areas.

Further, the device of the invention is a new measuring instrument to calculate the risk for developing coronary heart disease.

The following Examples represent preferred embodiments of the invention.

EXAMPLE 1

The following study was carried out to analyze the performance of the cardiovascular risk device of the invention for clinical and epidemiological purposes. Specifically, the bias and variability of the crossed and pointed values of glucose, age, systolic- and diastolic blood pressure, body mass index (BMI), HDL cholesterol, triglycerides and Total cholesterol were investigated.

Referring to the accompanying FIGS. 1 and 2, the following patient was analyzed for cardiovascular risk employing the cardiovascular risk device 10 shown in FIG. 1. The patient, a male of 55 years, had a systolic pressure of 158 mmHg, a diastolic pressure of 102 mmHg, a height of 1.70 m and weight of 83.8 kg. His plasma total cholesterol was 340 mg/dl, HDL-cholesterol 34 mg/dl and triglycerides 175 mg/dl. His glycemic value was 76 mg/dl. The patient did not smoke. As seen in FIG. 2, these values were projected on each of the individual scales 14 to 30 of the cardiovascular risk device 10 of the invention, which scales are positioned in a radial way all converging to one central point 31.

The different axis were projected on different risk areas 32, 34, 36. The most external concentric area 32 is considered to be the normal one (outside dark (for example, green) area). Thus, the projected result which falls in that area can be considered as normal values. The second light (for example, orange) area 34 is considered as an area with an elevated risk. All values projected in that area must be considered as abnormal. The third concentric circle 36 (inside dark (for example, red) area) is considered as a very high risk area.

The threshold for each cardiovascular risk factor corresponding to the three cardiovascular risk areas are given in the following table.

TABLE 1

The threshold on the axes of the cardiovascular risk device of the invention corresponding to the three cardiovascular risk areas.

| Parameter | Low Risk Outer Dark Area | Medium Risk Middle White Area | High Risk Inner Dark Area |
| --- | --- | --- | --- |
| Glucose (mg/dl) | 70–110 | 110–140 | 140–200 |
| Smoking (# cig/day) | 0–0 | 1–20 | 20–50 |
| Age (yrs) | 20–50 | 50–80 | 80–110 |
| Systolic BP (mm Hg) | 110–140 | 140–160 | 160–220 |
| Diastolic BP (mm Hg) | 75–90 | 90–105 | 105–120 |
| *Wt. (kg)/Ht.$^2$ (m) | 15–25 | 25–30 | 30–45 |
| HDL Cholesterol (mg/dl) | 85–35 | 35–30 | 30–5 |
| Triglycerides (mg/dl) | 50–150 | 150–250 | 250–450 |
| Total Cholesterol (mg/dl) | 150–200 | 200–300 | 300–500 |

*or Body Mass Index

In the present example, it can be observed that only 2 cardiovascular risk factors are considered as normal in the patient, namely his glucose value and that he is a non-smoker. On the other hand, the patient in question has 7 elevated risk factors. As seen in FIG. 2, by recording each of the risk factors on the appropriate risk scale and connecting the different values, a polygonic graphic presentation 40 of the cardiovascular risk factors of the patient is obtained. Calculation of the area of enclosed surface 40 or the ratio of the area of enclosed surface 40 and the total area of the circle is an index of severity. In the present example, the relative area (ratio of the actual enclosed area and the total area of the circle) is 0.32. (=CVRM-score or relative area CVRM).

The corresponding score for developing a coronary heart disease using the Framingham model (5 years) and the WHO-Erica model are −1.74 and −3.76, respectively.

EXAMPLE 2

The following study was carried out to evaluate the cardiovascular risk device of the invention (hereinafter referred to as CVRM which is an abbreviation for Cardiovascular Risk Manager) as a tool in clinical and epidemiological studies and as a predictor for developing coronary heart disease (CHD).

Ninety-seven (97) patients were studied out of which were 57 hypertensive patients and 40 hyperlipemic patients. A mixture of untreated (28) and treated (69) patients was investigated. The hypertensive patients received beta blockers, ACE inhibitors, diuretics, calcium antagonists and no treatment. The hyperlipemic patients received statin, resins, fibrates and no treatment.

Some geometrical properties of the patient's CVRM profile were investigated. Specifically, the correlation was established between the relative area enclosed by the patient's profile, i.e. the ratio of the actual area and the total area of the circle shown in FIGS. 1 and 2, and the risk score calculated from the WHO-Erica Project, supra and the revised risk score from the Framingham study, supra. The WHO study evaluated the risk factors for 6-year CHD mortality in Europe, divided in four areas: North, West, East and South. The WHO score taken in the present study corresponds to the score for Western Europe shown in Table 6 of WHO-Erica Project, supra. In the Framingham study, formulas are provided to calculate the 5- and 10-year probability of CHD events. The Framingham score used here corresponds to their 5-year risk score.

The following expression were used. For the WHO score:

WHO score = −14.97+0.0996*AGE+0.0068*TOTCHOL+0.0175*SYSTBP+0.0223*BMI+0.6548*SMOKING(y/n).

The Framingham score is constructed in several steps. First, there is the age independent score equal to:

s = 11.1122−0.9119*log(SYSTBP)−0.2767*SMOKING(y/n)0.7181*log(TOTCHOL/HDL).

The effect of age is different for men and women, as is the effect of diabetes. For men, m = s −1.4792*log(AGE)−0.1759*DIABETES(y/n); for women m = s −5.8549+1.8515*log(AGE/74)$^2$−0.3758*DIABETES(y/n).

Using sigma = exp(−0.3155−0.2784*m) and mu = 4.4181+m, the Framingham score for prediction of 5-year CHD-incidence is equal to FRA score = (log(5)−mu)/sigma.

In the above expression, a patient was considered diabetic if his/her glucose level was 110 mg/dl or more. LVH (based on ECG criteria) is not recorded on the CVRM, so it was assumed for Framingham score, that none of the patients suffered from left ventricular hypertrophy.

Both scores can be positive or negative, they can be turned into probabilities by a transformation. For the WHO score the logistic transformation is used, that is the WHO probability for a CHD death at years following the measurements is equal to $$P_{WHO} = \exp(\text{WHO score})/(1 + \exp(\text{WHO score})).$$

The Framingham probability for a CHD event 5 years after the measurement is equal to $$P_{FRA} = 1 - \exp(-\exp(\text{FRA score})).$$

Descriptive statistics for the total group of patients are given in Table 2. Also, the relative CVRM area (CVRM % area) from the patient's risk profile, the WHO risk score and probability and the revised risk score and probability from the Framingham study are evaluated.

TABLE 2

| Parameter | N | Min | Median | Max | Mean | SD |
|---|---|---|---|---|---|---|
| Glucose (mg/dl) | 96 | 70.2 | 91.6 | 199.0 | 98.0 | 26.6 |
| Age (yrs) | 97 | 26.9 | 52.8 | 88.9 | 52.1 | 12.9 |
| Systolic BP (mm Hg) | 97 | 115.8 | 148.2 | 218.3 | 148.8 | 22.2 |
| Diastolic BP (mm Hg) | 97 | 75.1 | 89.5 | 119.8 | 90.4 | 10.8 |
| BMI | 97 | 19.2 | 27.0 | 44.1 | 27.6 | 5.4 |
| HDL cholesterol (mg/dl) | 95 | 22.0 | 51.6 | 84.7 | 54.2 | 18.3 |
| Triglycerides (mg/dl) | 97 | 51.0 | 124.5 | 445.2 | 143.9 | 84.3 |

TABLE 2-continued

| Parameter | N | Min | Median | Max | Mean | SD |
|---|---|---|---|---|---|---|
| Tot Cholesterol (mg/dl) | 97 | 151.7 | 238.1 | 497.2 | 248.4 | 63.2 |
| CVRM % area | 90 | 0.14 | 0.44 | 0.69 | 0.44 | 0.12 |
| score WHO | 97 | −7.5 | −5.0 | −0.6 | −4.8 | 1.5 |
| probability WHO | 97 | 0.00 | 0.01 | 0.36 | 0.02 | 0.05 |
| score Framingham | 94 | −10.1 | −3.2 | −1.4 | −3.5 | 1.4 |
| probability Framingham | 94 | 0.01 | 0.04 | 0.22 | 0.06 | 0.05 |

The scores (and probabilities) are compared in Table 3 between the hypertensive and hyperlipemic patients. Within these two groups the medically treated patients are compared with the non-treated patients.

TABLE 3

Descriptive statistics Of the risk scores calculated from the CVRM, the WHO study and the Framingham study. The patient population is subdivided according to pathology and intake of medication. Also the WHO and Framingham probabilities for CHD events are calculated. The abbreviations HT, HL indicate the group of hypertensive patients and the group of hyperlipemic patients, respectively. P(H), P(M) stand for the significance of pathology, medication, respectively in the Two-way nested ANOVA.

| Parameter | GRP | N | Min | Median | Max | Mean | SD | P |
|---|---|---|---|---|---|---|---|---|
| CVRM % area | HT, NO MEDIC | 18 | 0.16 | 0.38 | 0.56 | 0.37 | 0.12 | |
| | HT, MEDIC | 37 | 0.14 | 0.43 | 0.65 | 0.42 | 0.11 | P(H) = 0.004 |
| | HL, NO MEDIC | 9 | 0.28 | 0.40 | 0.62 | 0.46 | 0.12 | |
| | HL, MEDIC | 26 | 0.24 | 0.48 | 0.69 | 0.49 | 0.09 | P(M) = 0.16 |
| score WHO | HT, NO MEDIC | 18 | −7.51 | −5.13 | −2.55 | −5.16 | 1.48 | |
| | HT, MEDIC | 39 | −7.33 | −4.19 | −1.86 | −4.33 | 1.41 | P(H) = 0.79 |
| | HL, NO MEDIC | 10 | −7.22 | −4.99 | −1.13 | −4.55 | 2.12 | |
| | HL, MEDIC | 130 | −7.23 | −5.16 | −0.58 | −5.13 | 1.24 | P(M) = 0.08 |
| probability WHO | HT, NO MEDIC | 18 | 0.001 | 0.006 | 0.073 | 0.015 | 0.022 | |
| | HT, MEDIC | 39 | 0.001 | 0.015 | 0.135 | 0.028 | 0.035 | |
| | HL, NO MEDIC | 10 | 0.001 | 0.008 | 0.245 | 0.046 | 0.077 | |
| | HL, MEDIC | 30 | 0.001 | 0.006 | 0.360 | 0.019 | 0.065 | |
| score Framingham | HT, NO MEDIC | 17 | −10.13 | −3.35 | −1.40 | −3.90 | 2.33 | P(H) = 0.98 |
| | HT, MEDIC | 38 | −6.02 | −3.15 | −1.40 | −3.23 | 1.07 | |
| | HL, NO MEDIC | 10 | −6.16 | −3.14 | −1.81 | −3.69 | 1.55 | P(M) = 0.25 |
| | HL, MEDIC | 29 | −7.19 | −3.47 | −1.75 | −3.41 | 1.14 | |
| probability Framingham | HT, NO MEDIC | 17 | 0.000 | 0.035 | 0.219 | 0.064 | 0.074 | |
| | HT, MEDIC | 38 | 0.002 | 0.042 | 0.218 | 0.059 | 0.051 | |
| | HL, NO MEDIC | 10 | 0.002 | 0.045 | 0.151 | 0.052 | 0.051 | |
| | HL, MEDIC | 25 | 0.001 | 0.035 | 0.159 | 0.050 | 0.045 | |

In Table 4, the Spearman correlations between the three risk scores calculated in the total patient population are shown overall and in the four subgroups according to pathology and intake of medication.

TABLE 4

| GROUP | | CORRELATION (P(CORRELATION)) | | |
|---|---|---|---|---|
| MEDIC | PATHO | % area, WHO score | % area, FRA score | WHO score, FRA score |
| TOTAL | | −0.53 (<0.0001) | −0.74 (<0.0001) | 0.70 (<0.0001) |
| NO | HL | −0.85 (0.004) | −0.72 (0.03) | 0.87 (0.001) |
| NO | HT | −0.53 (0.02) | −0.82 (<0.0001) | 0.83 (0.0001) |
| YES | HL | −0.49 (0.01) | −0.64 (0.0006) | 0.54 (0.002) |
| YES | HT | −0.49 (0.002) | −0.82 (<0.0001) | 0.59 (<0.0001) |

The abbreviations HL and HT stand for hyperlipemic and hypertensive patients, respectively.

In the evaluation of the correlations of the CVRM score and the WHO and Framingham scores, it should be noted that the WHO and Framingham scores are based on different populations, predicting also different events at slightly different times. On the other hand, the CVRM score is population independent and pictorially represents the risk of a patient for a CHD event by the size of the area enclosed by the patient's risk profile; the smaller the size the higher the risk.

The correlation of the CVRM score with the Framingham score is −0.74. This is in absolute value of about the same size as the correlation of the WHO with the Framingham score. The correlation of the CVRM score with the WHO score is −0.53. The correlations found in the four subgroups are roughly of the same size. All correlations are of moderate size, but still they are all highly significant.

Only the CVRM score was able to detect a significant difference in means between the group of hypertensive and the group of hyperlipemic patients.

A physician may use the cardiovascular diagram as shown in FIG. 2 in which different cardiovascular reference values are shown to help decide which treatment to start and to evaluate the efficacy of the treatment.

A copy of the same diagram can be used to give to the patient. However, the lay-out can be only a symbolic one, just to inform the patient that for a specific risk factor, he has a problem. This will motivate the patient to better control his cardiovascular risk factors and to see his progression in function of time and therapeutic intervention.

EXAMPLE 3

Correlation of the CVRM score (ratio of area of enclosed surface 40 to total area to the circle in FIG. 2) with the Framingham score for men and for women are set out below.

These were calculated from a sampling of 7,195 cardiovascular patients. The 10-years risk is given:
For men:
3,293 cases
$P_{10y} = 0.4823 - 0.5769$ (relative area CVRM) = % risk of a man developing CHD within 10 years.
$r = -0.64$
$p < 0.0001$
$(-0.67 < R < 0.63) = 95\%$ Confidence interval.
For women:
3,902 cases
$P_{10y} = 0.3623 - 0.5932$ (relative area CVRM) = % risk of a woman developing CHD within 10 years.
$r = -0.7$
$p < 0.0001$
$(-0.71 < R < 0.68) = 95\%$ Confidence interval.

Thus, from the relative CVRM-surface, the real cardiovascular risk for developing a cardiovascular disease (here within 10 years) can be calculated.

Figure 3:
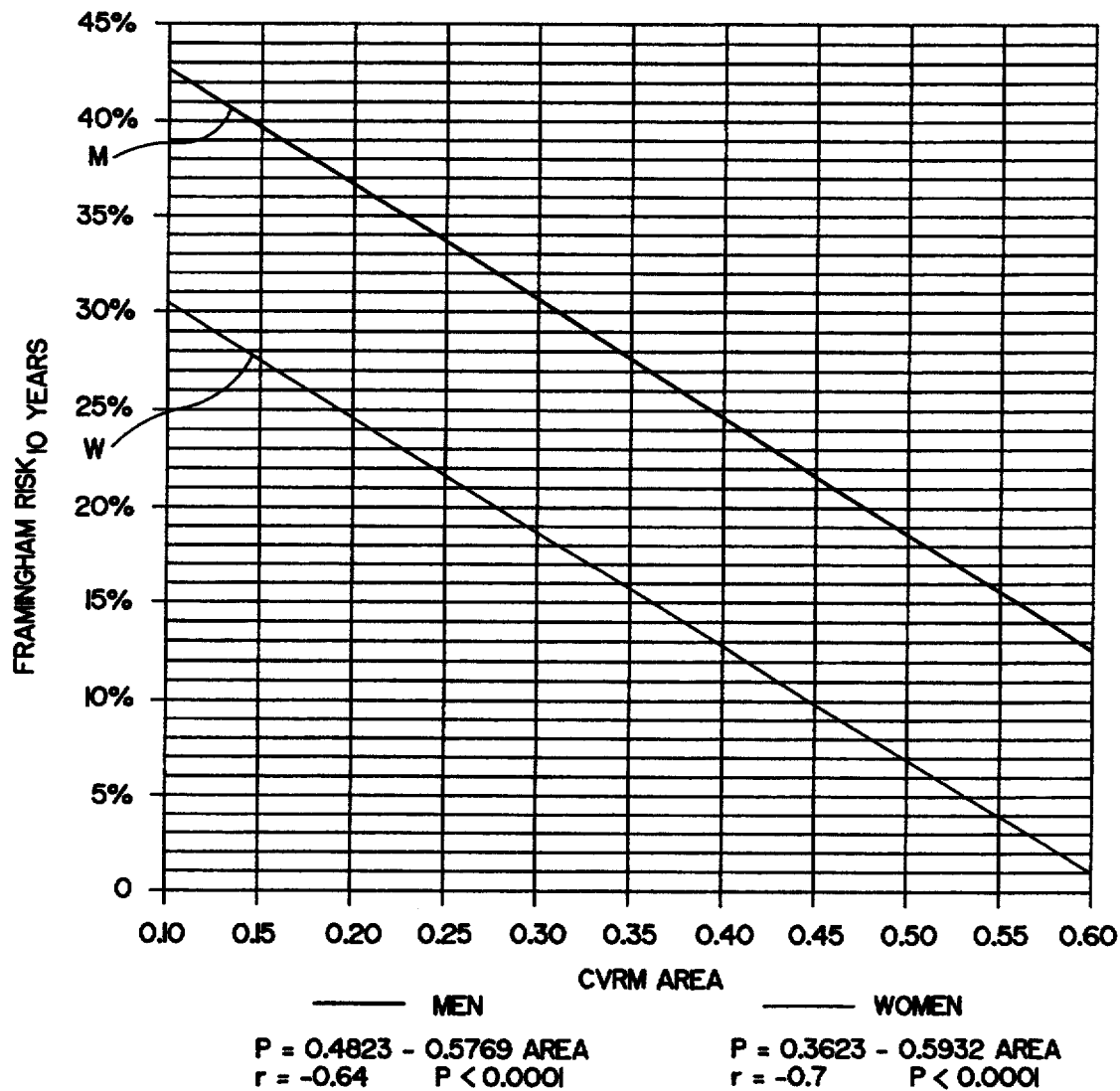
FIG. 3 is a graph of the correlation of CVRM area and Framingham Risk of cardiovascular disease over a ten (10) year period.

As seen in FIG. 3, the Framingham Risk over a 10 year period is plotted against the relative area CVRM (referred to in FIG. 3 as CVRM area). The line M is for men and the line W is for women.

Thus, for a man, as described in Example 1, having a CVRM area of 0.32, his risk of having cardiovascular disease within 10 years is about 29%.

For a woman having a CVRM area of 0.32, her risk of having a cardiovascular disease within 10 years is about 17%.

What is claimed is:

1. A method for calculating and visualising risk of developing coronary heart disease, which comprises providing a diagram which includes a series of cardiovascular risk areas delineating low to high risk areas, and a series of cardiovascular risk scales for various cardiovascular risk factors delineating low to high risk, superimposed over said cardiovascular risk areas; determining a numerical value for each cardiovascular risk factor of a patient, represented on the cardiovascular risk scales; recording such numerical value on an appropriate cardiovascular risk scale as a data point; connecting data points on adjacent cardiovascular risk scales to form an enclosed area of a patient superimposed on the cardiovascular risk areas, comparing the enclosed area superimposed on the cardiovascular risk areas against total area of the cardiovascular risk areas to determine a score of cardiovascular risk.

2. The method as defined in claim 1 including the step of providing in the diagram a series of cardiovascular risk areas formed of a series of concentric cardiovascular risk areas.

3. The method as defined in claim 2 including the step of comparing the enclosed area of the patient superimposed on the cardiovascular risk areas against an enclosed area of the total concentric cardiovascular risk areas to obtain a score of cardiovascular risk.

4. The method as defined in claim 3 including the step of correlating the cardiovascular risk area to Framingham risk for 10 year using period:
For Males
$P = 0.4823 - 0.5769$ (cardiovascular risk area)
For Females
$P = 0.3623 - 0.5932$ (cardiovascular risk area).

5. The method as defined in claim 2 including the step of delineating the concentric cardiovascular risk areas by different shades or colors.

6. The method as defined in claim 1 including the step of determining cardiovascular risk factors which include one or more of age, weight, blood pressure (systolic and diastolic), lipid parameters including total cholesterol, triglycerides, low density lipoproteins, high density lipoproteins, glycemic parameters and smoking habits.

* * * * *